US009643357B2

(12) United States Patent
Farah et al.

(10) Patent No.: US 9,643,357 B2
(45) Date of Patent: May 9, 2017

(54) ELECTROPHOTOGRAPHY-BASED ADDITIVE MANUFACTURING WITH POWDER DENSITY DETECTION AND UTILIZATION

(71) Applicant: Stratasys, Inc., Eden Prairie, MN (US)

(72) Inventors: Zeiter S. Farah, Minneapolis, MN (US); J. Samuel Batchelder, Somers, NY (US)

(73) Assignee: Stratasys, Inc., Eden Prairie, MN (US)

( * ) Notice: Subject to any disclaimer, the term of this patent is extended or adjusted under 35 U.S.C. 154(b) by 417 days.

(21) Appl. No.: 14/218,114

(22) Filed: Mar. 18, 2014

(65) Prior Publication Data
US 2015/0266236 A1   Sep. 24, 2015

(51) Int. Cl.
| | | |
|---|---|---|
| B29C 65/00 | (2006.01) | |
| B29C 67/00 | (2017.01) | |
| G01N 27/22 | (2006.01) | |
| G01R 1/18 | (2006.01) | |
| G03G 15/22 | (2006.01) | |
| B33Y 10/00 | (2015.01) | |
| B33Y 30/00 | (2015.01) | |
| B29L 31/00 | (2006.01) | |

(52) U.S. Cl.
CPC ......... *B29C 67/0051* (2013.01); *G01N 27/22* (2013.01); *G01R 1/18* (2013.01); *G03G 15/224* (2013.01); *B29L 2031/00* (2013.01); *B33Y 10/00* (2014.12); *B33Y 30/00* (2014.12)

(58) Field of Classification Search
CPC ......... G01R 1/18; G03G 15/224; G01N 27/22
See application file for complete search history.

(56) References Cited

U.S. PATENT DOCUMENTS 2,297,691 A    10/1942  Carlson
3,247,455 A *  4/1966  Benson, Jr. ............ G01B 7/087
                                                    193/37

(Continued)

FOREIGN PATENT DOCUMENTS

CN    101310964 A    11/2008
EP      0712051 A2    5/1996

(Continued)

OTHER PUBLICATIONS

"Xerography", Aug. 27, 2010, pp. 1-4, http:/en.wikipedia.org/wiki/Xerography.

(Continued)

*Primary Examiner* — Matthew Daniels
(74) *Attorney, Agent, or Firm* — Westman, Champlin & Koehler, P.A.

(57) ABSTRACT

An additive manufacturing system for printing a three-dimensional part, which includes one or more electrophotography engines configured to develop layers of the three-dimensional part, a rotatable transfer belt configured to receive the developed layers from the electrophotography engine(s), a detector configured to measure powder densities of the developed layers on the rotatable transfer belt, and to transmit signals relating to the measured powder densities to a controller assembly, and a printing assembly configured to receive the developed layer from the rotatable transfer belt and to print the three-dimensional part from the developed layers.

19 Claims, 9 Drawing Sheets

(56) References Cited

U.S. PATENT DOCUMENTS

| | | | |
|---|---|---|---|
| 4,752,727 A * | 6/1988 | Schneider | G01P 5/18 324/178 |
| 4,988,602 A | 1/1991 | Jongewaard et al. | |
| 5,088,047 A | 2/1992 | Bynum | |
| 5,099,288 A | 3/1992 | Britto et al. | |
| 5,254,421 A | 10/1993 | Coppens et al. | |
| 5,354,414 A | 10/1994 | Feygin | |
| 5,354,799 A | 10/1994 | Bennett et al. | |
| 5,514,232 A | 5/1996 | Burns | |
| 5,592,266 A | 1/1997 | Park et al. | |
| 5,593,531 A | 1/1997 | Penn | |
| 5,594,652 A | 1/1997 | Penn et al. | |
| 5,764,521 A | 6/1998 | Batchelder et al. | |
| 5,866,058 A | 2/1999 | Batchelder et al. | |
| 5,981,616 A | 11/1999 | Yamamura et al. | |
| 5,990,268 A | 11/1999 | Dickens, Jr. et al. | |
| 6,052,551 A | 4/2000 | De Cock et al. | |
| 6,066,285 A | 5/2000 | Kumar | |
| 6,085,957 A | 7/2000 | Zinniel et al. | |
| 6,169,605 B1 | 1/2001 | Penn et al. | |
| 6,206,672 B1 * | 3/2001 | Grenda | B29C 67/0074 264/484 |
| 6,329,115 B1 | 12/2001 | Yamashita | |
| 6,376,148 B1 | 4/2002 | Liu et al. | |
| 6,492,651 B2 | 12/2002 | Kerekes | |
| 6,509,128 B1 | 1/2003 | Everaerts et al. | |
| 6,531,086 B1 | 3/2003 | Larsson | |
| 6,780,368 B2 | 8/2004 | Liu et al. | |
| 6,799,959 B1 | 10/2004 | Tochimoto et al. | |
| 6,815,636 B2 | 11/2004 | Chung et al. | |
| 6,887,640 B2 | 5/2005 | Zhang et al. | |
| 7,011,783 B2 | 3/2006 | Fong | |
| 7,077,638 B2 | 7/2006 | Leyden et al. | |
| 7,208,257 B2 | 4/2007 | Cheng et al. | |
| 7,261,541 B2 | 8/2007 | Fong | |
| 7,261,542 B2 | 8/2007 | Hickerson et al. | |
| 7,291,242 B2 | 11/2007 | Khoshnevis | |
| 7,435,763 B2 | 10/2008 | Farr et al. | |
| 7,815,826 B2 | 10/2010 | Serdy et al. | |
| 7,988,906 B2 | 8/2011 | Monsheimer et al. | |
| 8,047,251 B2 | 11/2011 | Khoshnevis | |
| 8,119,053 B1 | 2/2012 | Bedal et al. | |
| 8,123,999 B2 | 2/2012 | Priedeman, Jr. et al. | |
| 8,124,192 B2 | 2/2012 | Paasche et al. | |
| 8,147,910 B2 | 4/2012 | Kritchman | |
| 8,173,258 B2 | 5/2012 | Monsheimer et al. | |
| 8,216,757 B2 | 7/2012 | Mizutani et al. | |
| 8,221,671 B2 | 7/2012 | Hull et al. | |
| 8,222,908 B2 | 7/2012 | Paul et al. | |
| 8,246,888 B2 | 8/2012 | Hopkins et al. | |
| 8,249,480 B2 | 8/2012 | Aslam et al. | |
| 8,459,280 B2 | 6/2013 | Swanson et al. | |
| 2002/0014116 A1 * | 2/2002 | Campbell | A01D 33/00 73/149 |
| 2002/0093115 A1 | 7/2002 | Jang et al. | |
| 2002/0145213 A1 | 10/2002 | Liu et al. | |
| 2003/0087176 A1 | 5/2003 | Ezenyilimba et al. | |
| 2004/0173946 A1 | 9/2004 | Pfeifer et al. | |
| 2004/0232583 A1 | 11/2004 | Monsheimer et al. | |
| 2005/0207801 A1 | 9/2005 | Kunii et al. | |
| 2005/0218549 A1 | 10/2005 | Farr et al. | |
| 2008/0032083 A1 | 2/2008 | Serdy et al. | |
| 2008/0169585 A1 | 7/2008 | Zinniel | |
| 2008/0169589 A1 | 7/2008 | Sperry et al. | |
| 2008/0171284 A1 | 7/2008 | Hull et al. | |
| 2008/0226346 A1 | 9/2008 | Hull et al. | |
| 2009/0236775 A1 | 9/2009 | Monsheimer et al. | |
| 2011/0117485 A1 | 5/2011 | Hermann et al. | |
| 2011/0186081 A1 | 8/2011 | Dunn et al. | |
| 2011/0190446 A1 | 8/2011 | Matsui et al. | |
| 2011/0222884 A1 | 9/2011 | Hirayama et al. | |
| 2012/0041132 A1 | 2/2012 | Monsheimer et al. | |
| 2012/0139167 A1 | 6/2012 | Fruth et al. | |
| 2012/0201960 A1 | 8/2012 | Hartmann et al. | |
| 2012/0202012 A1 | 8/2012 | Grebe et al. | |
| 2012/0237870 A1 | 9/2012 | Watanabe et al. | |
| 2012/0263488 A1 | 10/2012 | Aslam et al. | |
| 2012/0274002 A1 | 11/2012 | Uchida | |
| 2013/0075013 A1 | 3/2013 | Chillscyzn et al. | |
| 2013/0077996 A1 | 3/2013 | Hanson et al. | |
| 2013/0077997 A1 | 3/2013 | Hanson et al. | |
| 2013/0078013 A1 * | 3/2013 | Chillscyzn | B29C 67/0074 399/307 |
| 2013/0171434 A1 | 7/2013 | Hirth et al. | |
| 2013/0186549 A1 | 7/2013 | Comb et al. | |
| 2013/0186558 A1 | 7/2013 | Comb et al. | |
| 2014/0004462 A1 | 1/2014 | Zaretsky | |
| 2014/0167326 A1 | 6/2014 | Jones et al. | |
| 2016/0161872 A1 * | 6/2016 | Orrock | G03G 9/0819 264/484 |

FOREIGN PATENT DOCUMENTS

| | | |
|---|---|---|
| GB | 2446386 A | 8/2008 |
| JP | 5165350 A | 7/1993 |
| JP | 8281808 A | 10/1996 |
| JP | 2001075376 A | 3/2001 |
| JP | 2002347129 A | 12/2002 |
| JP | 2003053849 A | 2/2003 |
| JP | 2003071940 A | 3/2003 |
| JP | 2005062860 A | 3/2005 |
| JP | 2006182813 A | 7/2006 |
| WO | 9851464 A1 | 11/1998 |
| WO | 2007114895 A2 | 10/2007 |
| WO | 2011065920 A1 | 6/2011 |
| WO | 2012034666 A1 | 3/2012 |

OTHER PUBLICATIONS

Jones, Jason, "Selective Laser Printing", Published Prior to Jan. 14, 2013, 1 page.

International Search Report and Written Opinion dated Jun. 30, 2015, for corresponding International Application No. PCT/US2015/017978, filed Feb. 27, 2015.

* cited by examiner

US 9,643,357 B2

ELECTROPHOTOGRAPHY-BASED ADDITIVE MANUFACTURING WITH POWDER DENSITY DETECTION AND UTILIZATION

BACKGROUND

The present disclosure relates to additive manufacturing systems and processes for printing three-dimensional (3D) parts and support structures. In particular, the present disclosure relates to additive manufacturing systems and processes for building 3D parts and support structures using an imaging process, such as electrophotography.

Additive manufacturing systems (e.g., 3D printers) are used to build 3D parts from digital representations of the 3D parts (e.g., AMF and STL format files) using one or more additive manufacturing techniques. Examples of commercially available additive manufacturing techniques include extrusion-based techniques, ink jetting, selective laser sintering, powder/binder jetting, electron-beam melting, and stereolithographic processes. For each of these techniques, the digital representation of the 3D part is initially sliced into multiple horizontal layers. For each sliced layer, a tool path is then generated, which provides instructions for the particular additive manufacturing system to form the given layer.

For example, in an extrusion-based additive manufacturing system, a 3D part or model may be printed from a digital representation of the 3D part in a layer-by-layer manner by extruding a flowable part material. The part material is extruded through an extrusion tip carried by a print head of the system, and is deposited as a sequence of roads on a substrate in an x-y plane. The extruded part material fuses to previously deposited part material, and solidifies upon a drop in temperature. The position of the print head relative to the substrate is then incremented along a z-axis (perpendicular to the x-y plane), and the process is then repeated to form a 3D part resembling the digital representation.

In fabricating 3D parts by depositing layers of a part material, supporting layers or structures are typically built underneath overhanging portions or in cavities of objects under construction, which are not supported by the part material itself. A support structure may be built utilizing the same deposition techniques by which the part material is deposited. The host computer generates additional geometry acting as a support structure for the overhanging or free-space segments of the 3D part being formed, and in some cases, for the sidewalls of the 3D part being formed. The support material adheres to the part material during fabrication, and is removable from the completed 3D part when the printing process is complete.

In two-dimensional (2D) printing, electrophotography (i.e., xerography) is a technology for creating 2D images on planar substrates, such as printing paper and transparent substrates. Electrophotography systems typically include a conductive support drum coated with a photoconductive material layer, where latent electrostatic images are formed by electrostatic charging, followed by image-wise exposure of the photoconductive layer by an optical source. The latent electrostatic images are then moved to a developing station where toner is applied to charged areas, or alternatively to discharged areas of the photoconductive insulator to form visible images. The formed toner images are then transferred to substrates (e.g., printing paper) and affixed to the substrates with heat and/or pressure.

SUMMARY

An aspect of the present disclosure is directed to an additive manufacturing system for printing a 3D part. The system includes one or more electrophotography engines configured to develop layers of the 3D part, and a rotatable transfer belt configured to receive the developed layers from the electrophotography engine(s). The system also includes a detector configured to measure powder densities of the developed layers on the rotatable transfer belt, and to transmit signals relating to the measured powder densities to a controller assembly of the system. Furthermore, the system includes a printing assembly (e.g., a layer transfusion assembly) configured to receive the developed layer from the rotatable transfer belt and to print the 3D part from the developed layers.

Another aspect of the present disclosure is directed to a method for printing a 3D part with an additive manufacturing system. The method includes producing a developed layer of a part material with an electrophotography engine of the additive manufacturing system, and transferring the developed layer from the electrophotography engine to a transfer belt of the additive manufacturing system. The method also includes rotating the transfer belt with the developed layer, measuring a powder density of the developed layer on the rotating transfer belt, heating the developed layer on the rotating transfer belt after measuring the powder density, and pressing the heated developed layer into contact with a top surface of the 3D part.

Another aspect of the present disclosure is directed to a method for measuring a powder density of a developed layer, and utilizing the measured part density, in an additive manufacturing system. The method includes rotating a transfer belt of the additive manufacturing system, measuring one or more capacitance values of the rotating transfer belt in a clean state, and determining a baseline capacitance value from the one or more measured capacitance values for the rotating transfer belt. The method also includes producing the developed layer of a powder-based material with an electrophotography engine of the additive manufacturing system, transferring the developed layer from the electrophotography engine to the rotating transfer belt, and measuring one or more capacitance values of the developed layer on the rotating transfer belt. The method further includes determining a sample capacitance value the one or more measured capacitance values for the developed layer on the rotating transfer belt, and determining a difference between the sample capacitance value and the baseline capacitance value.

DEFINITIONS

Unless otherwise specified, the following terms as used herein have the meanings provided below:

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the inventive scope of the present disclosure.

Directional orientations such as "above", "below", "top", "bottom", and the like are made with reference to a direction along a printing axis of a 3D part. In the embodiments in which the printing axis is a vertical z-axis, the layer-printing direction is the upward direction along the vertical z-axis. In these embodiments, the terms "above", "below", "top", "bottom", and the like are based on the vertical z-axis. However, in embodiments in which the layers of 3D parts are printed along a different axis, the terms "above", "below", "top", "bottom", and the like are relative to the given axis.

The term "providing", such as for "providing a material" and the like, when recited in the claims, is not intended to require any particular delivery or receipt of the provided item. Rather, the term "providing" is merely used to recite items that will be referred to in subsequent elements of the claim(s), for purposes of clarity and ease of readability.

Unless otherwise specified, temperatures referred to herein are based on atmospheric pressure (i.e. one atmosphere).

The terms "about" and "substantially" are used herein with respect to measurable values and ranges due to expected variations known to those skilled in the art (e.g., limitations and variabilities in measurements).

DETAILED DESCRIPTION

The present disclosure is directed to an electrophotography-based additive manufacturing system and process for measuring powder densities for developed layers of part and support materials. During an electrophotography printing operation, one or more electrophotography (EP) engines may develop or otherwise image each layer of part and support materials using an electrophotographic process. The developed layers are then transferred to a layer transfusion assembly where they are transfused (e.g., using heat and/or pressure) to print one or more 3D parts and support structures in a layer-by-layer manner.

The part and support materials are powder-based materials charged triboelectrically through the mechanism of frictional-contact charging with carrier particles. This charging of the part or support material may be referred to by its triboelectric charge-to-mass (Q/M) ratio, which may be a positive or negative charge and has a desired magnitude. The Q/M ratio is inversely proportional to the powder density of the part or support material, which can be referred to by its mass per unit area (M/A) value. As such, for a given applied development field, as the value of Q/M ratio of the part material is increased from a given value, the M/A value (i.e., the powder density) of the part or support material decreases, and vice versa.

In order to print 3D parts with good part strengths and accuracy, the powder density or M/A value is preferably maintained at a stable level during an entire printing operation. However, due to numerous processing conditions in the system, the powder densities of the developed layers can potentially fluctuate or otherwise drift from their intended levels. As such, the system discussed herein incorporates one or more detectors that measure the powder densities of developed layers during printing operations, preferably with the use of electrical fields, as discussed below. The detector(s) may then transmit signals to a controller assembly of the system, which may monitor the corresponding M/A values in order to identify any changes from the intended levels.

Figure 1:
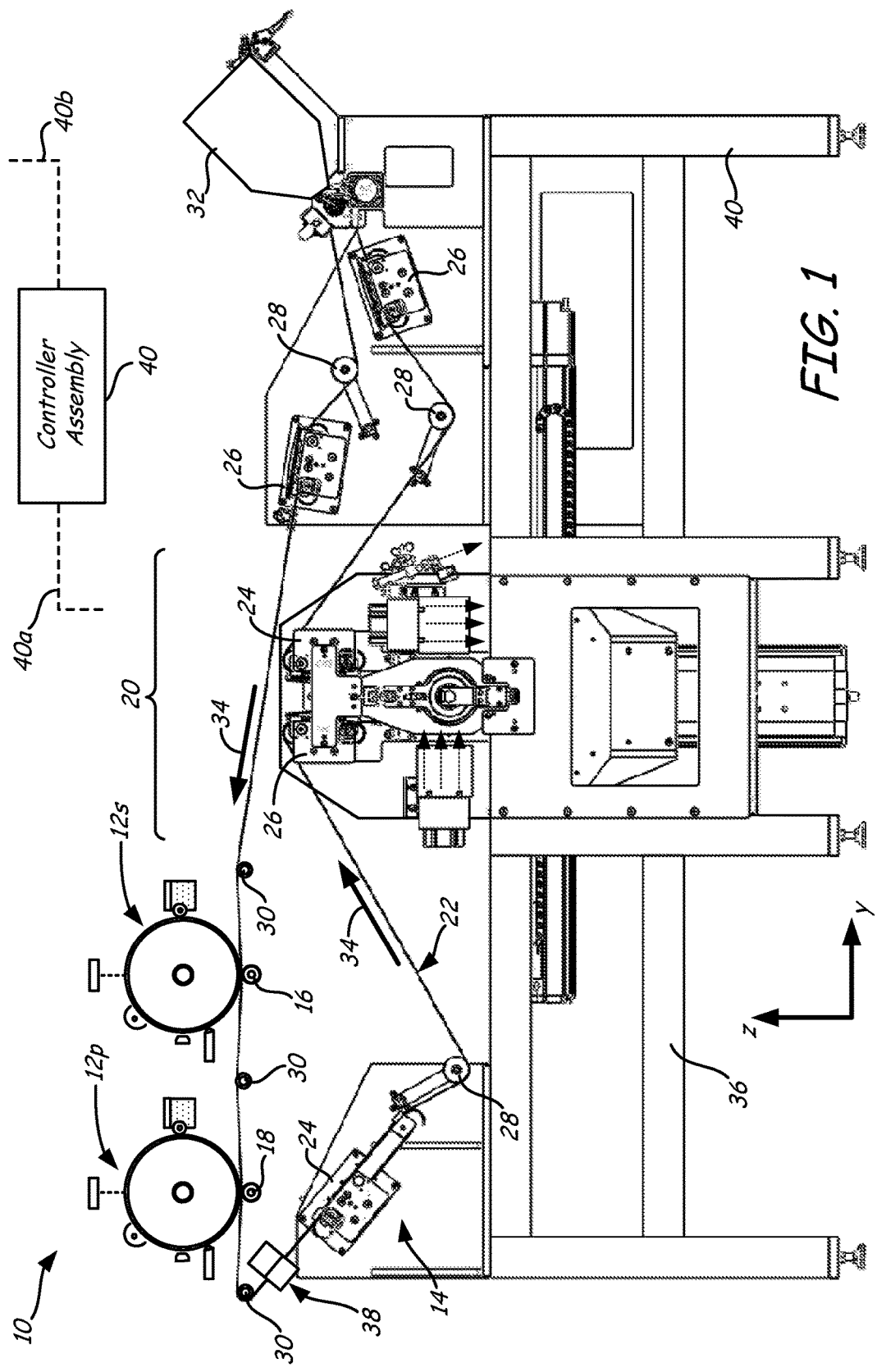
FIG. 1 is a front view of an example electrophotography-based additive manufacturing system for printing 3D parts and support structures with the use of a powder-density detector.

FIGS. 1-4 illustrate system 10, which is an example electrophotography-based additive manufacturing system for printing 3D parts from a part material, and associated support structures from a support material, and is designed to measure powder densities of developed layers during printing operations. As shown in FIG. 1, system 10 includes a pair of EP engines 12p and 12s, belt transfer assembly 14, biasing mechanisms 16 and 18, and layer transfusion assembly 20. Examples of suitable components and functional operations for system 10 include those disclosed in Hanson et al., U.S. Publication Nos. 2013/0077996 and 2013/0077997, in Comb et al., U.S. Publication Nos. 2013/0186549 and 2013/0186558.

EP engines 12p and 12s are imaging engines for respectively imaging or otherwise developing layers of the powder-based part and support materials. As discussed below, the imaged layers may then be transferred to belt transfer assembly 14 (or other transfer medium) with biasing mechanisms 16 and 18, and carried to layer transfusion assembly 20 to print the 3D parts and associated support structures in a layer-by-layer manner.

In the shown embodiment, belt transfer assembly 14 includes transfer belt 22, belt drive mechanisms 24, belt drag mechanisms 26, loop limit sensors 28, idler rollers 30, and belt cleaner 32, which are configured to maintain tension on belt 22 while belt 22 rotates in the rotational direction of arrows 34. In particular, belt drive mechanisms 24 engage and drive belt 22, and belt drag mechanisms 26 may function as brakes to provide a service loop design for protecting belt 22 against tension stress, based on monitored readings via loop limit sensors 28.

The components of system 10 may be retained by one or more frame structures, such as frame 36. Additionally, the components of system 10 are preferably retained within an enclosable housing (not shown) that prevents ambient light from being transmitted to the components of system 10 during operation.

System 10 also includes detector 38 and controller assembly 40, where detector 38 is an example non-contact detector for measuring powder densities of developed layers, as discussed below. In the shown embodiment, detector 38 is positioned along belt 22 downstream from EP engine 12p and the first idler roller 30, and upstream from the first belt drive mechanism 24. One or more detectors 38 may alternatively be located at any suitable point along belt 22 between EP engine 12p and layer transfusion assembly 20.

Controller assembly 40 is one or more computer-based systems configured to operate the components of system 10, including detector 38. Controller assembly 40 may communicate over communication line 40a with the various components of system 10, such as EP engines 12p and 12s, belt transfer assembly 14, biasing mechanisms 16 and 18, layer transfusion assembly 20, detector 38, and various other sensors, calibration devices, display devices, and/or user input devices.

Additionally, controller assembly 40 may also communicate over communication line 40b with external devices, such as other computers and servers over a network connection (e.g., a local area network (LAN) connection). While communication lines 40a and 40b are each illustrated as a single signal line, they may each include one or more electrical, optical, and/or wireless signal lines.

Preferably, the one or more computer-based systems of controller assembly 40 are internal to system 10, allowing a user to operate system 10 over a network communication line 40b, such as from an external computer in the same manner as a two-dimensional printer. Alternatively, controller assembly 40 may also include one or more external computer-based systems (e.g., desktop, laptop, server-based, cloud-based, tablet, mobile media device, and the like) that may communicate with the internal computer-based system(s) of controller assembly 40, as well as communicating over a network via communication line 40b. In this alternative embodiment, the processing functions of controller assembly 40 discussed below may be divided between the internal and external computer-based systems. In yet another alternative embodiment, the one or more computer-based systems of controller assembly 40 may all be located external to system 10 (e.g., one or more external computers), and may communicate with system 10 over communication line 40a.

Figure 2:
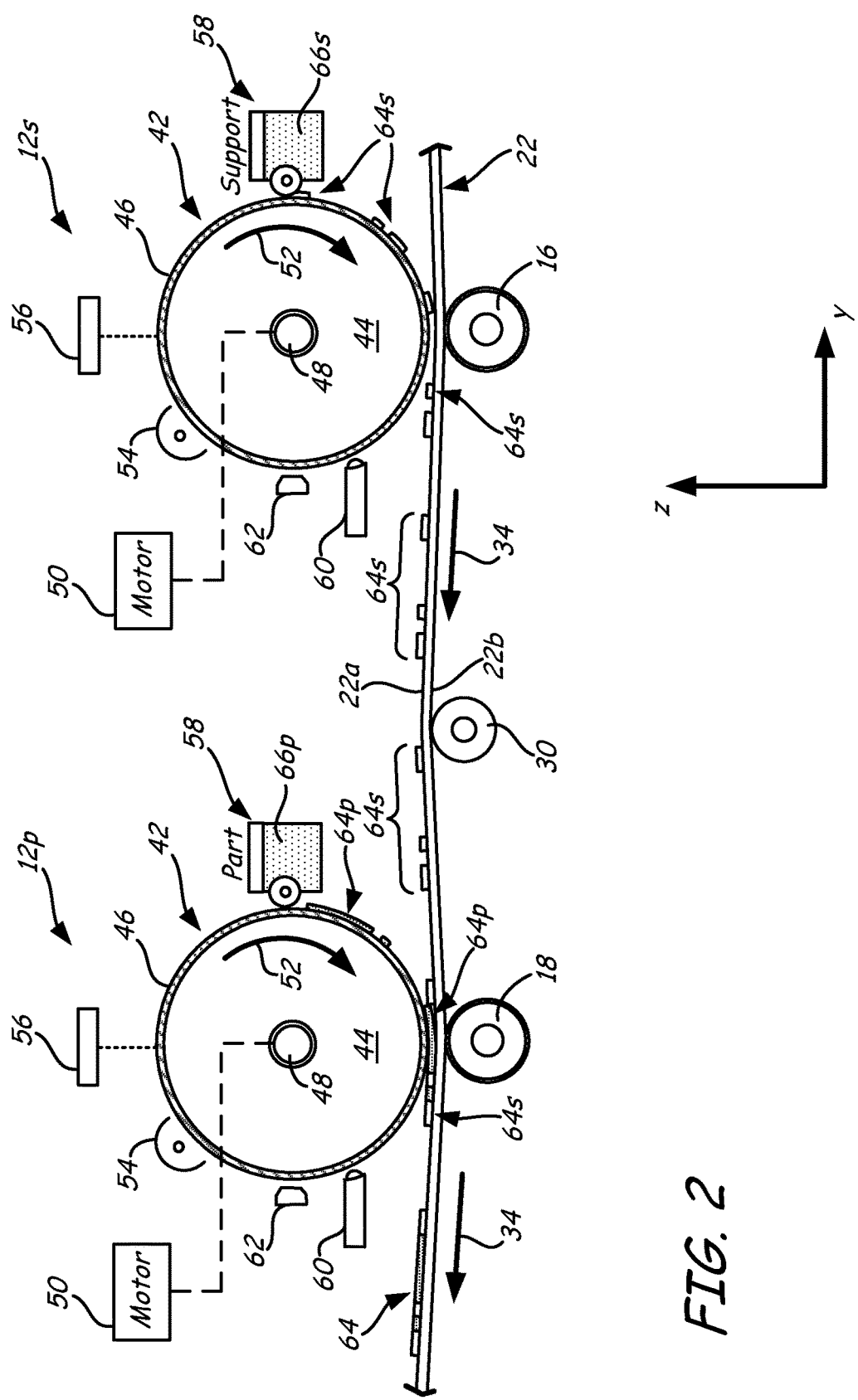
FIG. 2 is a schematic front view of a pair of electrophotography engines of the system for developing layers of the part and support materials.

FIG. 2 illustrates EP engines 12p and 12s, where EP engine 12s (i.e., the upstream EP engine relative to the rotational direction of belt 22) develops layers of the powder-based support material, and EP engine 12p (i.e., the downstream EP engine relative to the rotational direction of belt 22) develops layers of the powder-based part material. In alternative embodiments, the arrangement of EP engines 12p and 12s may be reversed such that EP engine 12p is upstream from EP engine 12s relative to the rotational direction of belt 22. In further alternative embodiments, system 10 may include three or more EP engines for printing layers of additional materials (e.g., materials of different colors, opacities, and/or functional characteristics).

In the shown embodiment, EP engines 12p and 12s may include the same components, such as photoconductor drum 42 having conductive drum body 44 and photoconductive surface 46. Conductive drum body 44 is an electrically-conductive drum (e.g., fabricated from copper, aluminum, tin, or the like) that is electrically grounded and configured to rotate around shaft 48. Shaft 48 is correspondingly connected to drive motor 50, which is configured to rotate shaft 48 (and photoconductor drum 42) in the direction of arrow 52 at a constant rate.

Photoconductive surface 46 is a thin film extending around the circumferential surface of conductive drum body 44, and is preferably derived from one or more photoconductive materials, such as amorphous silicon, selenium, zinc oxide, organic materials, and the like. As discussed below, surface 46 is configured to receive latent-charged images of the sliced layers of the 3D part or support structure (or negative images), and to attract charged particles of the part or support material of the present disclosure to the charged or discharged image areas based on the Q/M ratios of the materials, thereby creating the layers of the 3D part or support structure (and test samples, as discussed below).

As further shown, EP engines 12p and 12s each also include charge inducer 54, imager 56, development station 58, cleaning station 60, and discharge device 62, each of which may be in signal communication with controller assembly 40 over communication line 40a. Charge inducer 54, imager 56, development station 58, cleaning station 60, and discharge device 62 accordingly define an image-forming assembly for surface 46 while drive motor 50 and shaft 48 rotate photoconductor drum 42 in the direction of arrow 52.

In the shown example, the image-forming assembly for surface 46 of EP engine 12s is used to form layers 64s of the powder-based support material (referred to as support material 66s), where a supply of support material 66s may be retained by development station 58 (of EP engine 12s) along with carrier particles. Similarly, the image-forming assembly for surface 46 of EP engine 12p is used to form layers 64p of the powder-based part material (referred to as part material 66p), where a supply of part material 66p may be retained by development station 58 (of EP engine 12p) along with carrier particles.

As further discussed below, layers 64p and 64s may respectively include separate "test samples" of the part material 66p and support material 66s, where the test samples have defined and known dimensions, and provide convenient samples for detector 38 to measure for powder densities. In some embodiments, EP engines 12p and 12s may form these test samples for each layer 64p and each layer 64s. Alternatively, these test samples may be produced after a set number of layers 64p and 64s are developed, such as once per revolution of belt 22.

Charge inducer 54 is configured to generate a uniform electrostatic charge on surface 46 as surface 46 rotates in the direction of arrow 52 past charge inducer 54. Suitable devices for charge inducer 54 include corotrons, scorotrons, charging rollers, and other electrostatic charging devices.

Imager 56 is a digitally-controlled, pixel-wise light exposure apparatus configured to selectively emit electromagnetic radiation toward the uniform electrostatic charge on surface 46 as surface 46 rotates in the direction of arrow 52 past imager 56. The selective exposure of the electromagnetic radiation to surface 46 preferably corresponds to associated bitslices received from controller assembly 40 over communication line 40a, and causes discrete pixel-wise locations of the electrostatic charge to be removed (i.e., discharged to ground), thereby forming latent image charge patterns on surface 46.

Suitable devices for imager 56 include scanning laser (e.g., gas or solid state lasers) light sources, light emitting diode (LED) array exposure devices, and other exposure device conventionally used in 2D electrophotography systems. In alternative embodiments, suitable devices for charge inducer 54 and imager 56 include ion-deposition systems configured to selectively directly deposit charged ions or electrons to surface 46 to form the latent image charge pattern. As such, as used herein, the term "electrophotography" includes ionography.

As discussed below, in some embodiments, imager 56 includes an LED array exposure device, where controller assembly 40 may use the M/A values measured by detector 38 to calibrate the LED array (or sub-sets of LEDs in the LED array). Furthermore, controller assembly 40 may adjust a global imaging on-time for the entire LED array, or generate an individual imaging on-time-register for each LED in the LED array.

Each development station 58 is an electrostatic and magnetic development station or cartridge that retains the supply of part material 66p or support material 66s, preferably in powder form, along with carrier particles. Development stations 58 may function in a similar manner to single or dual component development systems and toner cartridges used in 2D electrophotography systems. For example, each development station 58 may include an enclosure for retaining the part material 66p or support material 66s and carrier particles. When agitated, the carrier particles generate triboelectric charges to attract the powders of the part material 66p or support material 66s, which charges the attracted powders to a desired sign and magnitude based on their Q/M ratios.

Each development station 58 may also include one or more devices for transferring the charged part material 66p or support material 66s to surface 46, such as conveyors, fur brushes, paddle wheels, rollers, and/or magnetic brushes. For instance, as surface 46 (containing the latent charged image) rotates from imager 56 to development station 58 in the direction of arrow 52, the charged part material 66p or support material 66s is attracted to the appropriately charged regions of the latent image on surface 46, utilizing either charged area development or discharged area development (depending on the electrophotography mode being utilized).

This creates successive layers 64p or 64s as photoconductor drum 12 continues to rotate in the direction of arrow 52, where the successive layers 64p or 64s correspond to the successive bitslices of the digital model of the 3D part or support structure (and the test samples). After being developed, the successive layers 64p or 64s are then rotated with surface 46 in the direction of arrow 52 to a transfer region in which layers 64p or 64s are successively transferred from photoconductor drum 42 to belt 22. While illustrated as a direct engagement between photoconductor drum 42 and belt 22, in some preferred embodiments, EP engines 12p and 12s may also include intermediary transfer drums and/or belts, as discussed further below in FIG. 3.

After a given layer 64p or 64s is transferred from photoconductor drum 42 to belt 22 (or an intermediary transfer drum or belt), drive motor 50 and shaft 48 continue to rotate photoconductor drum 42 in the direction of arrow 52 such that the region of surface 46 that previously held the layer 64p or 64s passes cleaning station 60. Cleaning station 60 is a station configured to remove any residual, non-transferred portions of part or support material 66p or 66s. Suitable devices for cleaning station 60 include blade cleaners, brush cleaners, electrostatic cleaners, vacuum-based cleaners, and combinations thereof.

After passing cleaning station 60, surface 46 continues to rotate in the direction of arrow 52 such that the cleaned regions of surface 46 pass discharge device 62 to remove any residual electrostatic charge on surface 46, prior to starting the next cycle. Suitable devices for discharge device 62 include optical systems, high-voltage alternating-current corotrons and/or scorotrons, one or more rotating dielectric rollers having conductive cores with applied high-voltage alternating-current, and combinations thereof.

Transfer belt 22 is a transfer medium for transferring the developed successive layers 64p and 64s from photoconductor drum 42 (or an intermediary transfer drum or belt) to layer transfusion assembly 20. Examples of suitable transfer belts for belt 22 include those disclosed in Comb et al., U.S. Publication Nos. 2013/0186549 and 2013/0186558. Belt 22 includes front surface 22a and rear surface 22b, where front surface 22a faces surfaces 46 of photoconductor drums 42 and rear surface 22b is in contact with biasing mechanisms 16 and 18.

Biasing mechanisms 16 and 18 are configured to induce electrical potentials through belt 22 to electrostatically attract layers 64p and 64s from EP engines 12p and 12s to belt 22. Because layers 64p and 64s are each only a single layer increment in thickness at this point in the process, electrostatic attraction is suitable for transferring layers 64p and 64s from EP engines 12p and 12s to belt 22.

Controller assembly 40 preferably rotates photoconductor drums 42 of EP engines 12p and 12s at the same rotational rates that are synchronized with the line speed of belt 22 and/or with any intermediary transfer drums or belts. This allows system 10 to develop and transfer layers 64p and 66s in coordination with each other from separate developer images. In particular, as shown, each part layer 64p may be transferred to belt 22 with proper registration with each support layer 64s to preferably produce a combined or composite part and support material layer 64.

This allows layers 64p and 64s to be transfused together, requiring the part and support materials to have thermal properties and melt rheologies that are similar or substantially the same. As can be appreciated, some layers transferred to layer transfusion assembly 20 may only include support material 66s or may only include part material 66p, depending on the particular bitslices that are transmitted to each of EP engines 12p and 12s.

In an alternative embodiment, part layers 64p and support layers 64s may optionally be developed and transferred along belt 22 separately, such as with alternating layers 64p and 64s. These successive, alternating layers 64p and 64s may then be transferred to layer transfusion assembly 20, where they may be transfused separately to print the 3D part and support structure.

Figure 3:
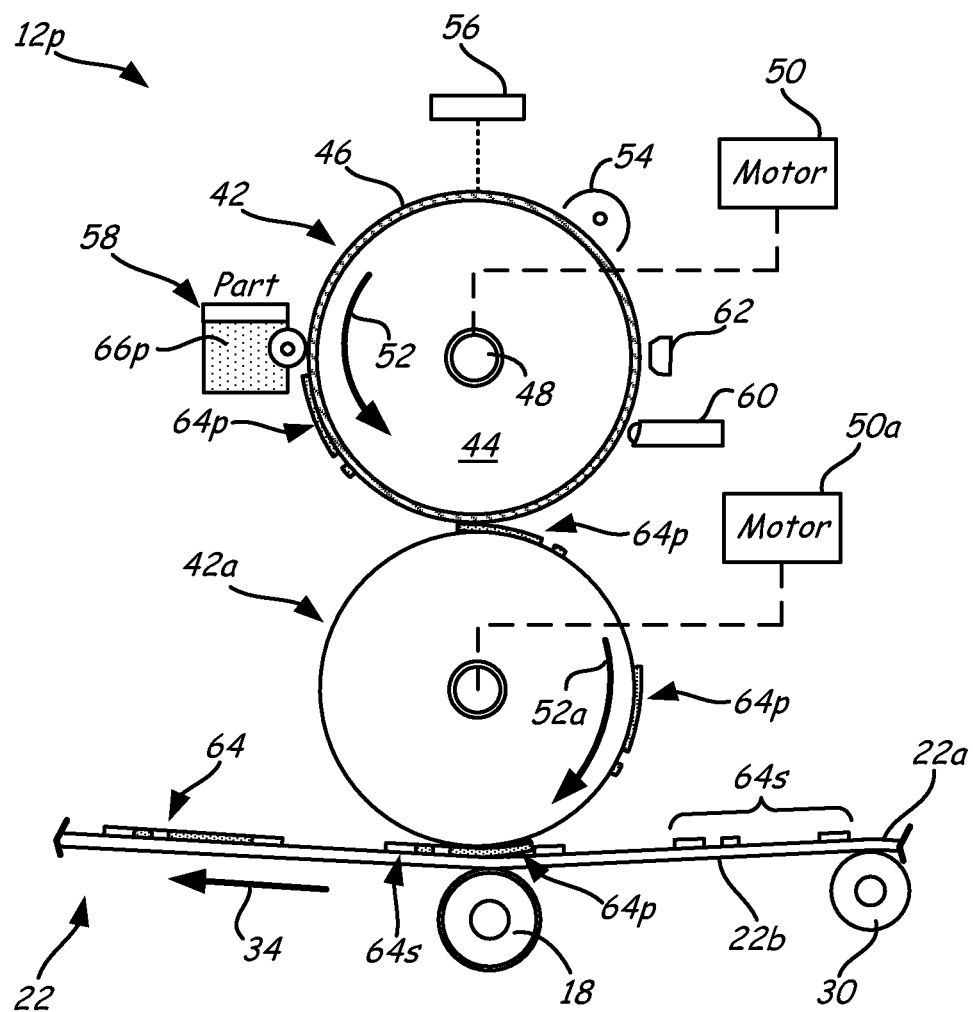
FIG. 3 is a schematic front view of an alternative electrophotography engine, which includes an intermediary drum or belt.

In some embodiments, one or both of EP engines 12p and 12s may also include one or more intermediary transfer drums and/or belts between photoconductor drum 42 and belt 22. For example, as shown in FIG. 3, EP engine 12p may also include intermediary drum 42a that rotates an opposing rotational direction from arrow 52, as illustrated by arrow 52a, under the rotational power of motor 50a. Intermediary drum 42a engages with photoconductor drum 42 to receive the developed layers 64p from photoconductor drum 42, and then carries the received developed layers 64p and transfers them to belt 22.

EP engine 12s may include the same arrangement of intermediary drum 42a for carrying the developed layers 64s from photoconductor drum 42 to belt 22. The use of such intermediary transfer drums or belts for EP engines 12p and 12s can be beneficial for thermally isolating photoconductor drum 42 from belt 22, if desired.

Figure 4:
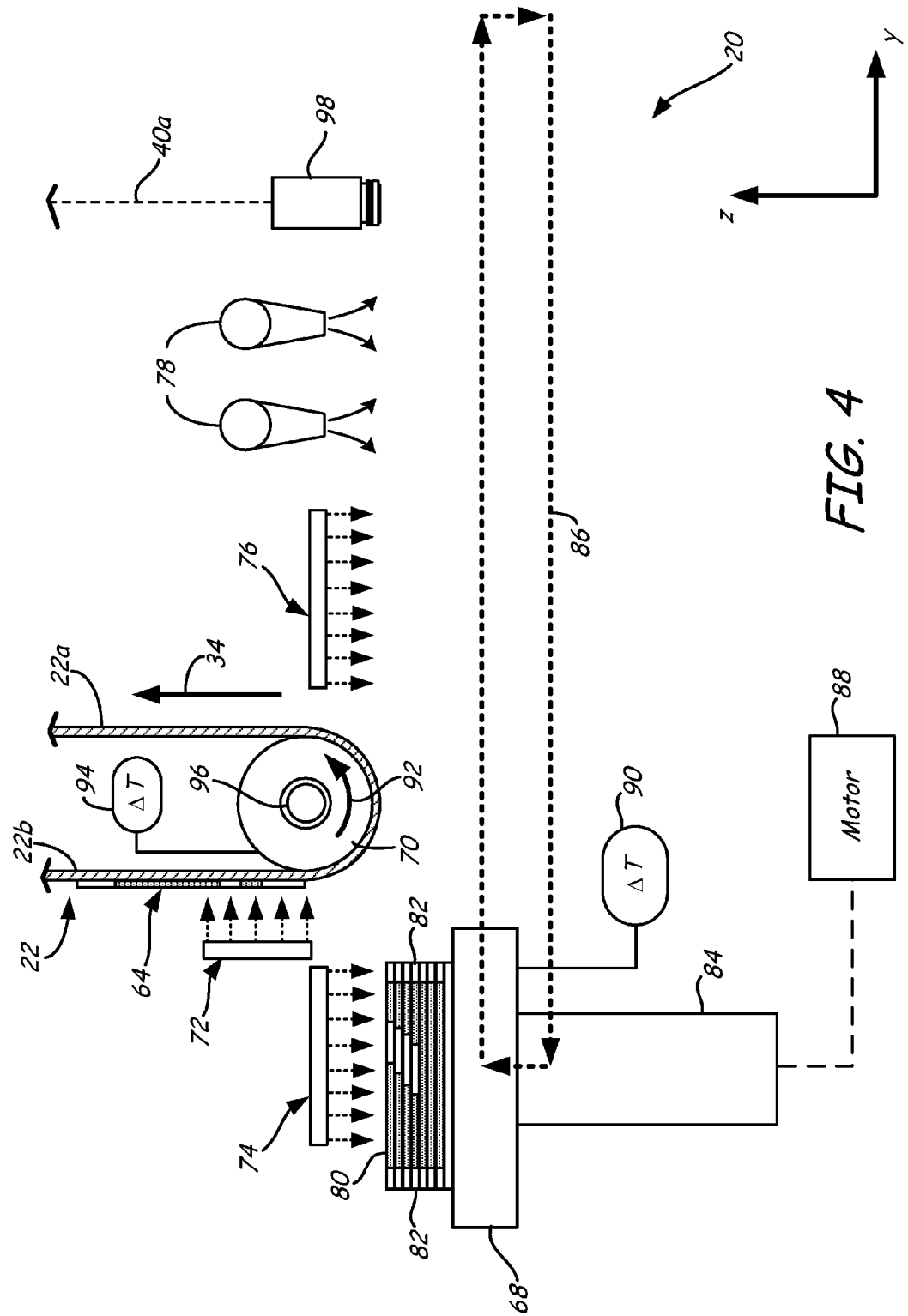
FIG. 4 is a schematic front view of a layer transfusion assembly of the system for performing layer transfusion steps with the developed layers.

FIG. 4 illustrates an example embodiment for layer transfusion assembly 20. As shown, layer transfusion assembly 20 is an example printing assembly that includes build platform 68, nip roller 70, heaters 72 and 74, post-fuse heater 76, and air jets 78 (or other cooling units). A suitable operation of layer transfusion assembly 20 is discussed in Comb et al., U.S. Publication Nos. 2013/0186549 and 2013/0186558, and in co-filed U.S. patent application Ser. No. 14/218,102, entitled "Electrophotography-Based Additive Manufacturing With Pre-Sintering.

Briefly, build platform 68 is a platform assembly or platen of system 10 that is configured to receive the heated combined layers 64 (or separate layers 64p and 64s) for printing a 3D part and support structure, referred to as 3D part 80 and support structure 82, in a layer-by-layer manner. In some embodiments, build platform 68 may include removable film substrates (not shown) for receiving the printed layers 64, where the removable film substrates may be restrained against build platform using any suitable technique (e.g., vacuum drawing, removable adhesive, mechanical fastener, magnetic attraction, and the like).

Build platform 68 is supported by gantry 84, which is a gantry mechanism configured to move build platform 68 along the z-axis and the y-axis, preferably to produce a reciprocating rectangular pattern, where the primary motion is back-and-forth along the y-axis (illustrated by broken lines 86). While the reciprocating rectangular pattern is described as a rectangular pattern with sharp axial corners (defined by arrows 86), gantry 84 may move build platform 68 in a reciprocating rectangular pattern having rounded or oval-defining corners, so long as build platform 68 moves along the y-axis during the pressing steps.

Gantry 84 may be operated by motor 88 based on commands from controller assembly 40, where motor 88 may be an electrical motor, a hydraulic system, a pneumatic system, or the like. In the shown embodiment, build platform 68 is heatable with heating element 90 (e.g., an electric heater), which is configured to heat and maintain build platform 68 at a desired elevated temperature.

Nip roller 70 is an example heatable element or heatable layer transfusion element, which is configured to rotate around a fixed axis with the movement of belt 22. In particular, nip roller 70 may roll against rear surface 22*b* in the direction of arrow 92 while belt 22 rotates in the direction of arrow 34. In the shown embodiment, nip roller 70 is heatable with heating element 94 (e.g., an electric heater). Heating element 94 is configured to heat and maintain nip roller 70 at a desired elevated temperature.

Heater 72 is one or more heating devices (e.g., an infrared heater and/or a heated air jet) configured to heat layers 64 to a desired elevated temperature prior to reaching nip roller 70. Each layer 64 desirably passes by (or through) heater 72 for a sufficient residence time to heat the layer 64 to the desired elevated temperature. Heater 74 is an optional heater that may function in the same manner as heater 72, and heats the top surfaces of 3D part 80 and support structure 82 to a desired elevated temperature. Post-fuse heater 76 is located downstream from nip roller 70 and upstream from air jets 78, and is configured to heat the transfused layers to a desired elevated temperature in the post-fuse or heat-setting step.

The desired elevated temperatures mentioned above may be independently selected and preset temperatures for transfusing the layers 64*p* and the support layers 64*s* together to the top surfaces of 3D part 80 and support structure 82 in a single transfusion step as combined or composite layers 64. Examples of suitable desired elevated temperatures for each step in layer transfusion assembly 20 include those discussed in Comb et al., U.S. Publication Nos. 2013/0186549 and 2013/0186558.

During the printing operation, belt 22 carries a layer 64 past heater 72, which may heat the layer 64 and the associated region of belt 22 to the desired elevated temperature. Correspondingly, gantry 84 may optionally move build platform 68 (with 3D part 80 and support structure 82) along the y-axis below, along, or through heater 74.

The continued rotation of belt 22 and the movement of build platform 68 align the heated layer 64 with the heated top surfaces of 3D part 80 and support structure 82, preferably with proper overlay in the x-y plane. Gantry 84 may continue to move build platform 68 along the y-axis, at a rate that is synchronized with the rotational rate of belt 22 in the direction of arrow 34 (i.e., the same directions and speed). This causes rear surface 22*b* of belt 22 to rotate around nip roller 70 to nip belt 22 and the heated layer 64 against the top surfaces of 3D part 80 and support structure 82. This presses the heated layer 64 between the heated top surfaces of 3D part 80 and support structure 82 at the location of nip roller 70, which at least partially transfuses heated layer 64 to the top layers of 3D part 80 and support structure 82.

As the transfused layer 64 passes the nip of nip roller 70, belt 22 wraps around nip roller 70 to separate and disengage from build platform 68. This assists in releasing the transfused layer 64 from belt 22, allowing the transfused layer 64 to remain adhered to 3D part 80 and support structure 82. After release, gantry 84 continues to move build platform 68 along the y-axis to post-fuse heater 76.

At post-fuse heater 76, the top-most layers of 3D part 80 and support structure 82 (including the transfused layer 64) may then be heated in a post-fuse or heat-setting step. This preferably melts the part and support materials of the transfused layer 64 to a highly fusible state such that polymer molecules of the transfused layer 64 quickly interdiffuse to achieve a high level of interfacial entanglement with 3D part 80 and support structure 82.

Additionally, as gantry 84 continues to move build platform 68 along the y-axis past post-fuse heater 76 to air jets 78, air jets 78 blow cooling air towards the top layers of 3D part 80 and support structure 82. This actively cools the transfused layer 64 down to the average part temperature, thereby preferably keeping 3D part 80 and support structure 82 at the average part temperature as also discussed in Comb et al., U.S. Publication Nos. 2013/0186549 and 2013/0186558.

Gantry 84 may then actuate build platform 68 downward, and move build platform 68 back along the y-axis to a starting position along the y-axis, following the reciprocating rectangular pattern 86. Build platform 68 desirably reaches the starting position for proper registration with the next layer 64. In some embodiments, gantry 84 may also actuate build platform 68 and 3D part 80/support structure 82 upward for proper overlay with the next layer 64. The same process may then be repeated for each remaining layer 64 of 3D part 80 and support structure 82.

As will become apparent from the discussion below, the test samples (not shown in FIG. 4) of layers 64 are preferably separate from 3D part 80 and support structure 82. As such, in embodiments in which the test samples are included with each developed layer 64, the test samples may also transfuse to each other to print separate towers of the part and support materials 66*p* and 66*s*. Alternatively, in embodiments in which the test samples are included after a set number of layers 64 are developed (e.g., once per revolution of belt 22), these test samples typically remain adhered to belt 22 at layer transfusion assembly, and may be removed with belt cleaner 32 and recycled or otherwise discarded in an environmentally-friendly manner.

As further shown in FIG. 4, in some embodiments, system 10 may also include one or more sensors configured to measure z-heights of the printed 3D part 80 and support structure 82 in real time while the layers 64 are printed, such as a pair of strain gauges 96 on the opposing ends of nip roller 70, and/or one or more imaging sensors 98 downstream from air jets 78 (or at any other suitable location along the movement path of build platform 68). Examples of suitable operations of strain gauges 96 and imaging sensors 98 are discussed in co-filed U.S. patent application Ser. No. 14/218,084, entitled "Additive Manufacturing With Virtual Planarization Control".

In embodiments that incorporate strain gauges 96 and/or imaging sensors 98, controller assembly 40 may also utilize the measured z-heights in combination with the measure M/A values from detector 38. For instance, z-height measurements provide layer heights, but do not directly account for layer densities. As such, coupling these z-height measurements with the powder densities of the developed layers can provide the densities of the printed layers of 3D part 80. This information can then be used to increase the strengths and qualities of 3D part 80, such as by calibration and/or real-time feedback control.

Figure 5:
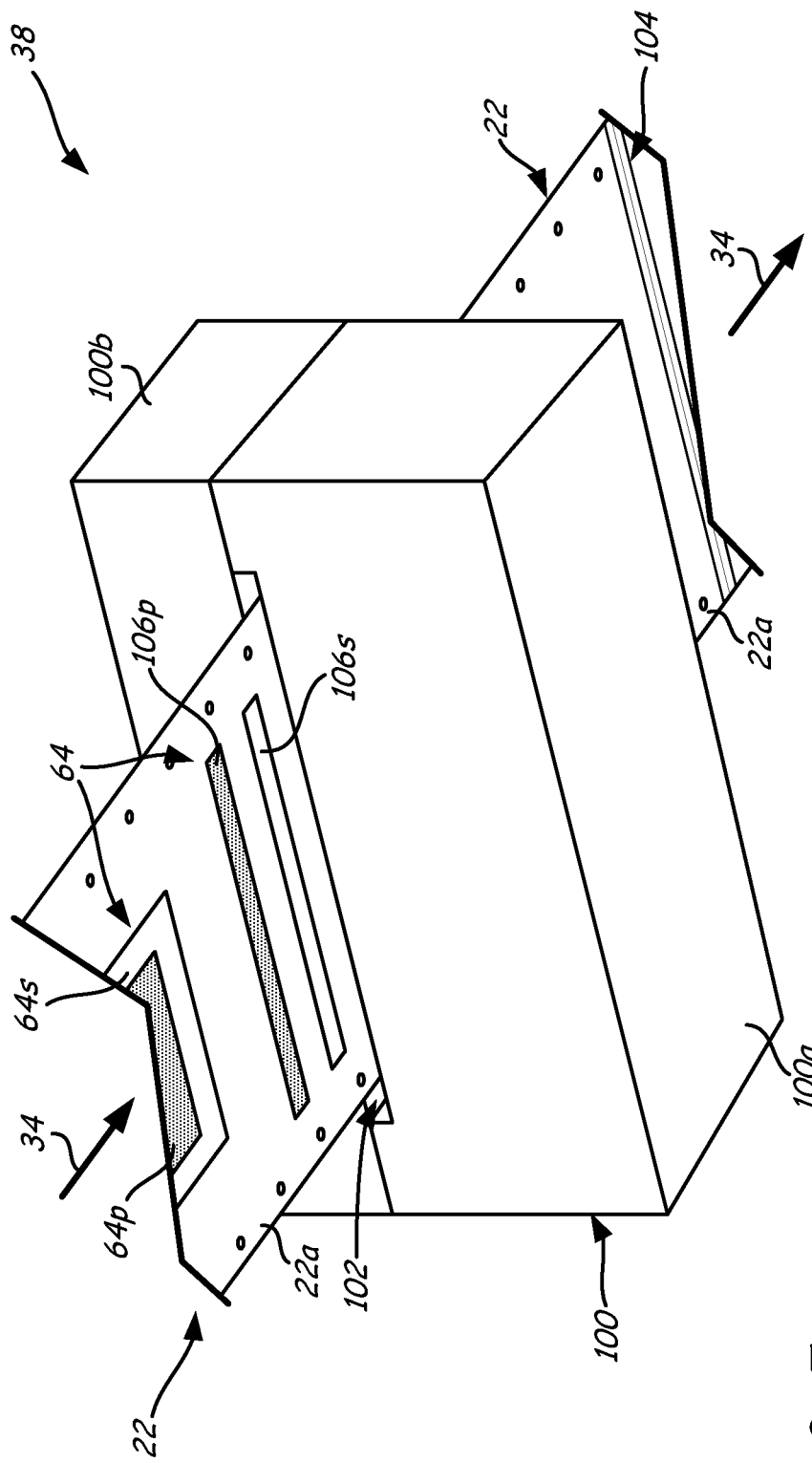
FIG. 5 is a bottom perspective view of the powder-density detector disposed along a rotatable transfer belt of the system.
Figure 6:
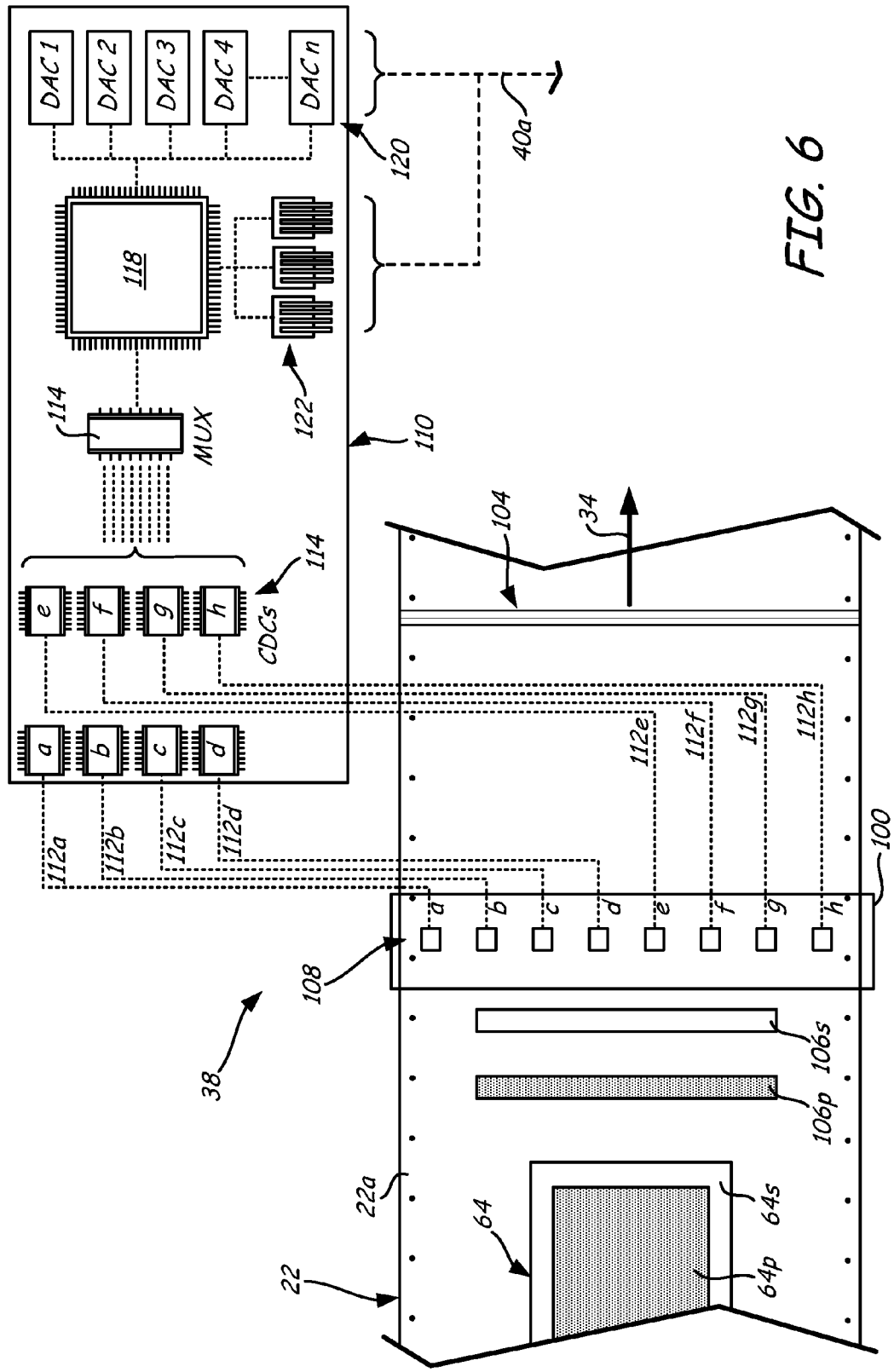
FIG. 6 is a bottom view of the powder-density detector and the rotatable transfer belt, where a control board of the powder-density detector is schematically illustrated.
Figure 7:
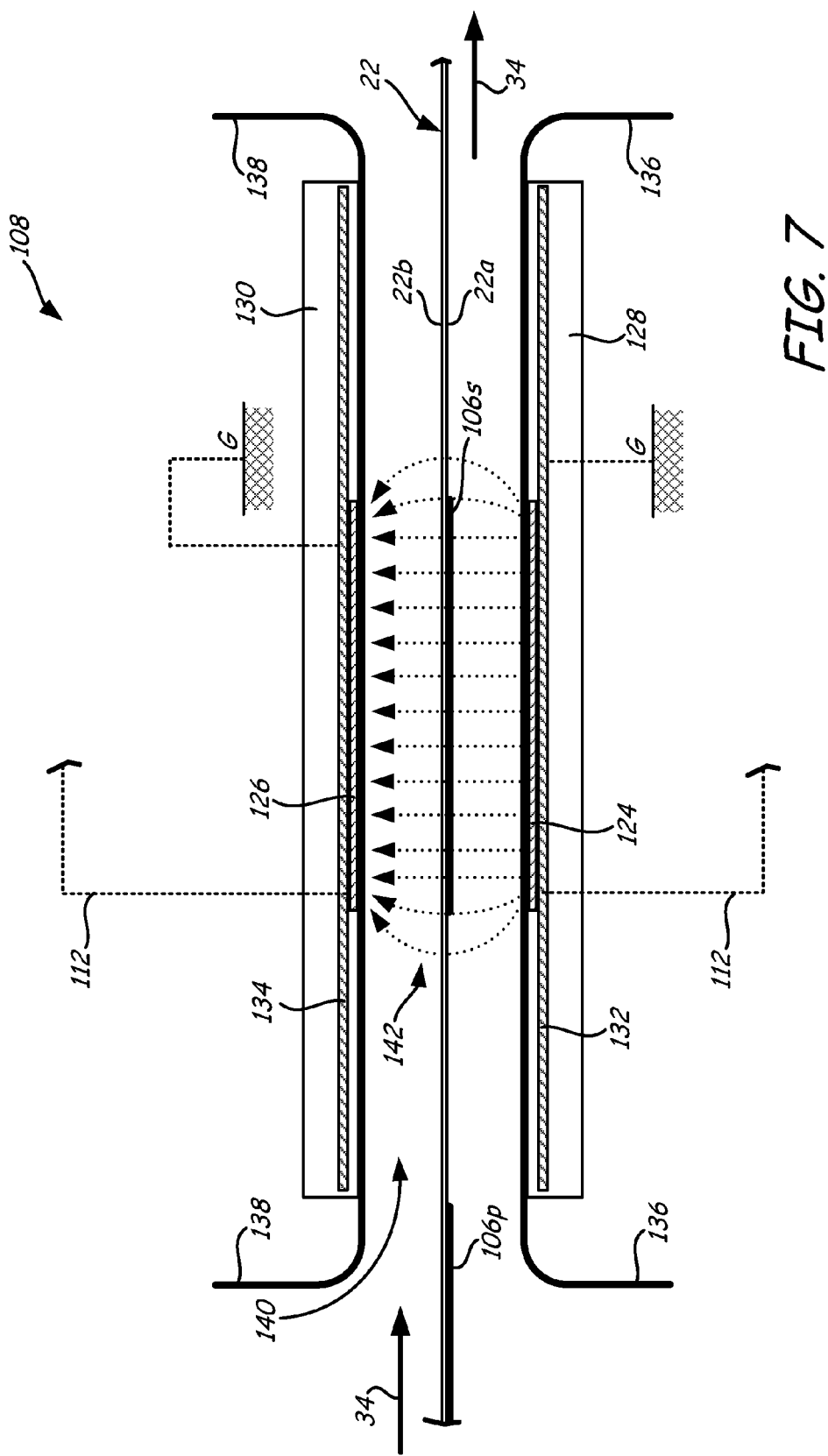
FIG. 7 is a side view of the powder-density detector in use with the rotatable transfer belt.

FIGS. 5-7 illustrate an example detector 38 for use in system 10, where detector 38 relies on capacitance sensing for measuring the powder densities of developed layers carried by belt 22. Detector 38 in this embodiment is preferably positioned along belt 22 between EP engines 12p and 12s and layer transfusion assembly 20, and more preferably closer to EP engines 12p and 12s than layer transfusion assembly 20 (e.g., as shown in FIG. 1).

As shown in FIG. 5, detector 38 includes an enclosed casing 100 having a slot 102 through which belt 22 and the developed layers 64 travel in the direction of arrow 34. Casing 100 is preferably a rigid housing derived from one or more materials that minimize penetration of external magnetic fields, and further provide physical protection to its internal components.

Various motors of system 10 (e.g., belt drive mechanisms 24 and gantry motor 88) can potentially generate magnetic fields with frequencies that can propagate through capacitance sensors of detector 38 to induce signal noise. Therefore, casing 100 preferably includes one or more magnetic shielding materials (e.g., mu-metal), which may be disposed between or laminated onto one or more rigid polymeric films. Casing 100 is also preferably operably secured (i.e., directly or indirectly secured) to frame 36 of system 10 to prevent detector 30 from shifting relative to belt 22 under operating vibrations from system 10.

As further shown, casing 100 may include multiple sub-casing shells, such as upper shell 100a and lower shell 100b, which are preferably securable together in a detatchable manner. Thus, while secured together, shells 100a and 100b are rigid and immovable relative to each other and frame 36, allowing belt 22 to pass freely through slot 102. However allowing shells 100a and 100b to detach and separate also allows belt 22 to be readily removed from detector 38, such as for replacement or maintenance.

Controller assembly 40 may divide belt 22 into multiple frames along its looped length, where each frame defines an area on which a developed layer 64 is carried between EP engines 12p and 12s and layer transfusion assembly 20. Belt 22 also includes seam 104, which connects the opposing ends of belt 22 into the continuous loop shown above in FIG. 1. As discussed below, detector 38 may use seam 104 as an index location along belt 22, and identify the location of each frame along belt 22 relative to seam 104 (as well as for belt speed monitoring).

As further shown in FIG. 5, layer 64 also includes test samples 106p and 106s adjacent to the layers 64p and 64s. In the shown embodiment, test sample 106p is a first bar-shaped test sample having predefined and known dimensions, and is developed by EP engine 12p with part material 66p. Similarly, test sample 106s is second a bar-shaped test sample having predefined and known dimensions, and is developed by EP engine 12s with support material 66s. Additional test samples of other materials may also be developed for each material used to print 3D part 80 and support structure 82 (e.g., a test sample may be printed for each EP engine used in system 10).

The predefined dimensions of test samples 106p and 106s assist the accuracy of the capacitance measurements by detector 38 since capacitance is dependent on the amount of material passing through an electrical field. In comparison, the dimensions of layers 64p and 64s will vary depending on the bitslice geometries of 3D part 80 and support structure 82, making it difficult to determine the powder densities or M/A values from the capacitance measurements.

As shown, test samples 106p and 106s are located upstream from layers 64p and 64s in the rotational direction of belt 22. Alternatively, one or both of test samples 106p and 106s may be located downstream from developed layer 64. Furthermore, while test sample 106s and is depicted as being upstream from test sample 106p, the reverse order may alternatively be used.

Controller assembly 40 may generate test samples 106p and 106s by modifying the bitslices used to generate layers 64p and 64s. For example, controller assembly 40 may add bitslice pixels for test samples 106p and 106s at coordinate locations that are outside the bounding boxes of layers 64p and 64s, but still within the usable build volume of system 10. As can be appreciated, the number of test samples 106p and 106s, and the number of corresponding measurements by detector 38 per rotation of belt 22 may vary as desired.

FIG. 6 illustrates the internal components of detector 38. As shown, detector 38 also includes a plurality of sensors 108 and control board 110, where control board 110 is illustrated schematically. Sensors 108 are preferably located within casing 100, and in some embodiments, control board 110 may also be located within casing 100.

In the shown example, sensors 108 include eight capacitance sensors, individually referred to as sensors 108a-108h, which are arranged as an array that is perpendicular to the movement direction of belt 22. In alternative embodiments, detector 38 may include fewer or more sensors 108, such that detector 38 includes at least one sensor 108, more preferably from two to ten sensors 108, and even more preferably from four to eight sensors 108.

Sensors 108a-108h are each configured to generate an electrical field that belt 22 passes through while moving in the direction of arrow 34 for measuring the capacitance of the generated electrical field. Belt 22, layers 64p and 64s, and test samples 106p and 106s that pass through sensors 108a-108h alter the effective capacitance of the electrical field as detected by sensors 108a-108h. As discussed below, these changes in the detected capacitance may be used by controller assembly 40 to measure the powder density (and M/A values) of the test samples 106p and 106s.

Sensors 108a-108h may communicate with control board 110 over electrical lines 112a-112h, where electrical lines 112a-112h are respectively coupled to capacitance-to-digital converters (CDCs) 114a-114h. In particular, sensors 108a-108h may transmit analog capacitance signals respectively over electrical lines 112a-112h, and CDCs 114a-114h respectively convert these received analog capacitance signals into digital signals.

The resulting digital signals are then relayed to multiplexer 116, which samples the received digital signals and relays them to microcontroller 118 for further signal processing. Microcontroller 118 then outputs the processed digital signals to one or more digital-to-analog converters (DACs) 120 and/or digital communication adapters 122, where DACs 120 and adapters 122 may each communicate with controller assembly 40 over communication line 40a.

DACs 12 allow detector 38 to output any desired analog signal combination from sensors 108a-108h. Correspondingly, adapters 122 allow detector 38 to output any desired digital signal combination from sensors 108a-108h. As discussed below controller assembly 40 may then use the analog and/or digital signals for a variety of different monitoring, calibration, and feedback controls.

As shown in FIG. 7, each sensor 108 preferably includes an excitation electrode 124, a sense electrode 126, respective support plates 128 and 130, respective shield ground plates 132 and 134, and respective insulating films 136 and 138. Excitation electrode 124 and sense electrode 126 are a pair of electrically-conductive electrodes that are offset from each other across a gap 140. This arrangement allows excitation electrode 124 and sense electrode 126 to function as a parallel-plate capacitor to generate an electrical field 142 across gap 140 when power is supplied to excitation electrode 124.

As can be appreciated, during a printing operation, various devices of system 10 can generate vibrations in frame 36, particularly gantry 84. As such, excitation electrode 124 and sense electrode 126 are preferably mounted within casing 100 in a rigid and fixed manner, such as with support plates 136 and 138 to ensure that the offset distance of gap 140 remains constant despite frame vibrations.

Shield ground plates 132 and 134 are grounding plates respectively secured to the back sides of excitation electrode 124 and sense electrode 126. Capacitance sensors 108 are sensitive to external electrical fields at their phase lock frequencies. As such, shield ground plates 132 and 134 guard excitation electrode 124 and sense electrode 126 from any external electrical fields by a ground connection with a low impedance path.

Additionally, the part and support materials carried by belt 22 can have spatially-varying potentials, such as up to about 400 Volts. As such, insulating film 136 is preferably secured between excitation electrode 124 and belt 22, and insulating film 138 is preferably secured between sense electrode 126 and belt 22. Suitable materials for insulating films 136 and 138 include polyimide films, such as polyimide tapes commercially available under the tradename "KAPTON" from E. I. du Pont de Nemours and Company, Wilmington, Del. This prevents sparks from jumping from belt 22 and/or the part and support materials to sensors 108.

To further assist in preventing this spark-over issue, gap 140 is preferably set as large as reasonably practical. Examples of suitable offset distances for gap 140 between excitation electrode 124 and sense electrode 126 range from about 0.06 inches to about 0.1 inches, and more preferably from about 0.07 inches to about 0.09 inches.

As further shown, belt 22 is positioned within gap 140, allowing test samples 106p and 106s to pass through the electrical fields 142 of sensors 108. As can be appreciated, the detected capacitance of electrical field 142 is affected by the thickness of belt 22 and the densities of test samples 106p and 106s. Thus, as belt 22 moves through gap 140 in the direction of arrow 34, when test sample 106s passes through the electrical fields 142 of sensors 108a-108h (as shown in FIG. 7), the overall dielectric constant between excitation electrode 124 and sense electrode 126 is increased by an amount that is proportional to the volume and density of the test sample 106s.

For example, without belt 22 or insulating films 136 and 138, the nominal capacitance $C_{nom}$ value between excitation electrode 124 and sense electrode 126 may be expressed by Equation 1:

$$C_{nom} = \frac{A}{d_{air}} \varepsilon_0 \varepsilon_{r,air} \quad \text{(Equation 1)}$$

where A is the overlapping surface area of excitation electrode 124 and sense electrode 126, $d_{air}$ is air gap distance between excitation electrode 124 and sense electrode 126, $\varepsilon_0$ is the electric constant (i.e., about 8.85 picoFarads/meter), and $\varepsilon_{r,air}$ is the dielectric constant of air (i.e., about 1). In the case in which excitation electrode 124 and sense electrode 126 each have a 0.5-inch surface area (that are directly opposite of each other), and an air gap distance of 0.085 inches, Equation 1 provides a nominal capacitance $C_{nom}$ value of 660 femtoFarads.

However, due to the inclusion of belt 22 and insulating films 136 and 138, Equation 1 may be modified to provide a baseline capacitance $C_{baseline}$ value, which is the capacitance without any part or support material on belt 22 (i.e., belt 22 is in a clean state) as shown in Equation 2:

$$C_{baseline} = \frac{A}{\frac{d_{air}}{\varepsilon_{r,air}} + \frac{d_{films}}{\varepsilon_{r,films}} + \frac{d_{belt}}{\varepsilon_{r,belt}}} \varepsilon_0 \quad \text{(Equation 2)}$$

where $d_{air}$ is adjusted air gap distance between excitation electrode 124 and sense electrode 126, $d_{films}$ is the combined thickness of insulating films 136 and 138, $d_{belt}$ is the thickness of belt 22, $\varepsilon_{r,films}$ is the dielectric constant of the material for insulating films 136 and 138, and $\varepsilon_{r,belt}$ is the dielectric constant of the material for belt 22.

As is understood, $d_{air}+d_{films}+d_{belt}$ equals the total gap distance between excitation electrode 124 and sense electrode 126. For instance, assuming belt 22 and insulating films 136 and 138 each have the same dielectric constant of 3.9, and each have a thickness of 0.005 inches, then Equation 2 provides a baseline capacitance $C_{baseline}$ value of 736 femtoFarads.

Correspondingly, when test sample 106p or 106s is carried by belt 22 through detector 38, the resulting sample capacitance $C_{sample}$ value can be shown by Equation 3:

$$C_{sample} = \frac{A}{\frac{d_{air}}{\varepsilon_{r,air}} + \frac{d_{films}}{\varepsilon_{r,films}} + \frac{d_{belt}}{\varepsilon_{r,belt}} + \frac{d_{test}}{\varepsilon_{r,test}}} \varepsilon_0 \quad \text{(Equation 3)}$$

where $d_{air}$ is adjusted air gap distance between excitation electrode 124 and sense electrode 126, $d_{test}$ is the thickness of test sample 106p or 106s, and $\varepsilon_{r,test}$ is the dielectric constant of the part or support material of test sample 106p or 106s. For instance, assuming the test sample 106p or 106s has a thickness of 15 micrometers, and a dielectric constant of 3.0, then Equation 3 provides a sample capacitance $C_{sample}$ value of 739 femtoFarads.

Comparing the results of Equations 2 and 3 provides a full-scale capacitance $C_f$ value of test sample 106p or 106s, as expressed by Equation 4:

$$C_f = C_{sample} - C_{baseline} \quad \text{(Equation 4)}$$

In the current example, Equation 4 provides a full-scale capacitance $C_f$ value for test sample 106p or 106s of about 3 femtoFarads. Accordingly, controller assembly 40 may determine the baseline capacitance $C_{baseline}$ from measured capacitance signals while belt 22 rotates in a clean state, may determine the sample capacitance $C_{sample}$ value from measured capacitance signals while belt 22 rotates with test sample 106p or 106s. From there, controller assembly 40 may determine the full-scale capacitance $C_f$ value as the difference between the sample capacitance $C_{sample}$ value and the baseline capacitance $C_{baseline}$ value, as shown in Equation 4.

Because the dimensions of test samples 106p and 106s are predetermined and known, controller assembly 40 may then associate this full-scale capacitance $C_f$ value with a particular powder density or M/A value. Subsequently measured capacitance signals that fluctuate or drift from this full-scale capacitance $C_f$ value may then be associated with changes in the powder density or M/A value, which can detrimentally affect part strengths and accuracies.

In comparison to the full-scale signal $C_f$, the noise-limited resolution of CDCs 114 sampling at 16 Hertz can achieve is about 34 attoFarads peak-to-peak, which is sufficiently signal resolution enough to detect capacitance changes from the full-scale signal $C_f$ of about 3 femtoFarads. For example, if belt 22 moves at a line speed of eight inches/second, test sample 106p or 106s will have a dwell time of 1/16 Hertz between excitation electrode 124 and sense electrode 126. This corresponds to M/A resolutions as low as 1% with a 0.5-inch spatial resolution, where additional static capacitance from fringing and guard fields can be nulled by microprocessor 118.

Seam 104 of belt 22 can have a thickness that is much greater than the average thickness of belt 22, which is detectable by detector 38. For example, seam 104 having twice the average thickness of belt 22 (e.g., 0.01 inches) produces a signal of about 25 femtoFarads. As such, detector 38 can readily recognize the location of seam 104 during every revolution of belt 22. This allows controller assembly 40 to use seam 104 as accurately measure the rotational speed of belt 22, as well as providing an index location for belt 22.

The above discussion is also based on the assumption that belt 22 has a constant thickness laterally and longitudinally. However, belt 22 can exhibit small thickness variations due to manufacturing limitations. As such, in some embodiments, detector 38 can also map the thickness of belt 22 while belt 22 rotates in the direction of arrow 34, and while no part or support materials are present (i.e., belt 22 is clean). In this case, sensors 108a-108h may measure the capacitance over multiple locations along the length of belt 22, indexed at seam 104.

For instance, sensors 108a-108h may measure the capacitance of belt 22 over every 0.25-inch or 0.5-inch increment along the length of belt 22, thereby providing eight lateral measurements for each longitudinal measurement. These measurements provide localized baseline capacitance $C_{baseline}$ values, and may then be relayed to controller assembly 40.

Controller assembly 40 may then create a thickness map for belt 22 that is indexed from seam 104. During a subsequent printing operation, controller assembly 40 may then compare these localized baseline capacitance $C_{baseline}$ values to the sample capacitance $C_{sample}$ values of test samples 106p and 106s depending on their relative locations along (or laterally across) belt 22. This can further increase the resolutions of the full-scale signals $C_f$ for test samples 106p and 106s.

Figure 8:
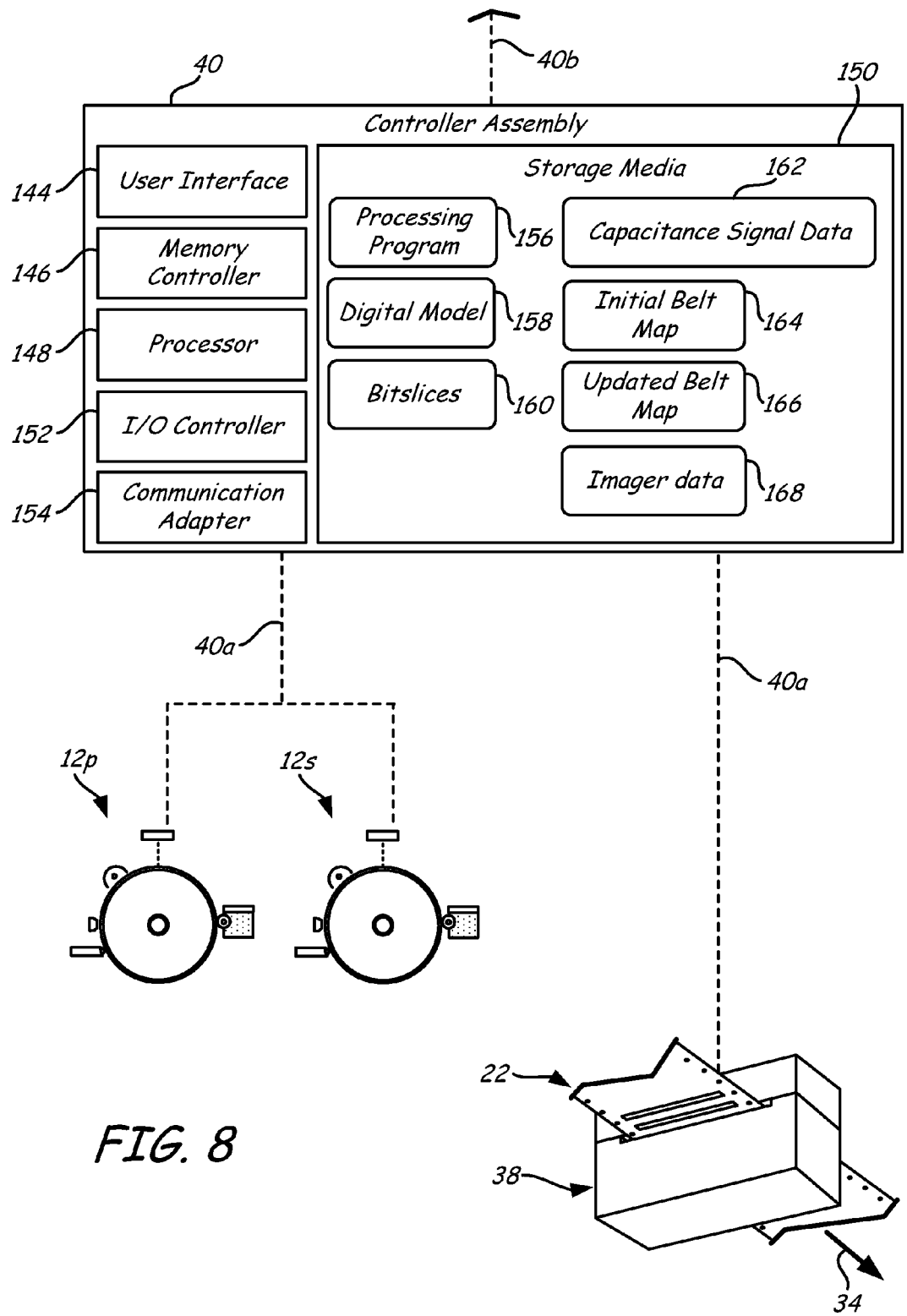
FIG. 8 is a schematic illustration of a controller assembly of the system in use with electrophotography engines and the powder-density detector.

As shown in FIG. 8, controller assembly 40 may include any suitable computer-based hardware, such as user interface 144, memory controller 146, processor 148, storage media 150, input/output (I/O) controller 152, and communication adapter 154. Controller assembly 40 may also include a variety of additional components that are contained in conventional computers, servers, media devices, and/or printer controllers.

User interface 144 is a user-operated interface (e.g., keyboards, touch pads, touch-screen displays, display monitors, and other eye, voice, movement, or hand-operated controls) configured to operate controller assembly 40. Memory controller 146 is a circuit assembly that interfaces the components of controller assembly 40 with one or more volatile random access memory (RAM) modules of storage media 150. Processor 148 is one or more computer-processing units configured to operate controller assembly 40, optionally with memory controller 146. For instance, processor 148 may include one or more microprocessor-based engine control systems and/or digitally-controlled raster imaging processor systems.

Storage media 150 is one or more internal and/or external data storage devices or computer storage media for controller assembly 40, such as volatile RAM modules, read-only memory modules, optical media, magnetic media (e.g., hard disc drives), solid-state media (e.g., FLASH memory and solid-state drives), analog media, and the like. Storage media 150 may retain an executable copy of processing program 156, one or more digital models 158 to be printed with system 10, and generated bitslices 160, each which may be utilized as disclosed in co-filed U.S. patent application Ser. No. 14/218,084, entitled "Additive Manufacturing With Virtual Planarization Control".

I/O controller 152 is a circuit assembly that interfaces memory controller 146, processor 148, and storage media 150 with various input and output components of controller assembly 40, including communication adapter 154. Communication adapter 154 is one or more wired or wireless transmitter/receiver adapters configured to communicate over communication lines 40a and 40b.

Controller assembly 40 may receive signals of the sample capacitance $C_{sample}$ values from detector 38 over communication line 40a, such as from DACs 120 and/or adapters 122 of detector 38, and store the received signals on storage media 150 as capacitance signal data 162. In embodiments in which controller assembly 40 receives the signals from DACs 120, controller assembly 40 preferably includes one or more analog-to-digital converters (not shown) to digitized the received analog signals for storage on storage media 150 and/or subsequent processing.

As mentioned above, controller assembly 40 may also create a thickness map for belt 22 from the localized baseline capacitance $C_{baseline}$ values, and which are indexed from seam 104. For instance, at the start up of a printing operation, controller assembly 40 may rotate belt 22 in the direction of arrow 34, and have detector 38 collect the localized baseline capacitance $C_{baseline}$ values prior to EP engines 12p and 12s operating. These localized baseline capacitance $C_{baseline}$ values may then be transmitted to controller assembly 40 and stored on storage media 150 as an initial belt map 164, which functions as the capacitance baseline for the localized points along belt 22, pursuant to Equation 2 shown above.

Additionally, after system 10 runs for a given duration, frame 36 can heat up due to the heating steps at layer transfusion assembly 20. Because of this temperature increase, the distance of gap 140 between excitation electrode 124 and sense electrode 126 can potentially increase, such as due to material expansions in casing 100. In fact, if the temperature increase is significant, gap 140 can swell by as much as 50% of the thickness of test samples 106a and 106b.

As such, after a given operating duration, controller assembly 40 preferably introduces one or more EP engine pauses to allow a clean belt 22 to rotate one or more full cycles past detector 38, as indexed by seam 104. Alternatively (or additionally), detector 38 may measure clean regions of belt 22 between the developed layers 64 to generate a liner dilation if the average baseline capacitance $C_{baseline}$ values deviate significantly from the values in initial belt map 164. For instance, controller assembly 40 may skip a particular frame location along belt 22 during each revolution to allow detector 38 to measure the clean belt 22 of the skipped frame location. The skipped frame location may then shift to the next adjacent frame location during the subsequent revolution, and so on.

Regardless of the technique used, these new localized baseline capacitance $C_{baseline}$ values may then be transmitted to controller assembly 40 and stored on storage media 150 as updated belt map 166, which may replace the values of initial belt map 164 as the capacitance baseline. Furthermore, these updates may be made periodically through the printing operation to maintain good signal-to-noise resolutions, and for system performance monitoring.

As discussed above, the capacitance signal data 162 may be used to measure the powder densities of the part and support materials 66p and 66 during printing operations, where capacitance signal fluctuations or drifts from the full-scale signals $C_f$ may identify powder density changes. If the measured capacitance signals increase, this can correspond to a decrease in powder density, and vice versa. These powder density or M/A values may be used for a variety of purposes, such as performance monitoring, calibration, and feedback controls.

For example, the measured powder densities may be used to modify the Q/M ratios of part material 66p and/or support material 66s to account for powder-density drifts over time. This can assist in stabilizing the powder densities of these materials.

In some embodiments, controller assembly 40 may also generate reports for the processing parameters of system 10, including the capacitance signal data 162, and the associated powder density or M/A values. This can assist with any potential processing or maintenance issues with system 10.

Additionally, as discussed above, in embodiments that incorporate strain gauges 96 and/or imaging sensors 98, controller assembly 40 may also utilize the measured z-heights in combination with the measure M/A values from detector 38. This combined information can then be used to increase the strengths and qualities of 3D part 80 and support structure 82, such as by calibration and/or real-time feedback control.

A particularly unique use of capacitance signal data 162 involves modifications to the LED arrays in imagers 56 of EP engines 12p and 12s. In this case, controller assembly 168 may also imager LED data 168, such as imaging on-time values for the LEDs, where imager data 168 may be stored on storage media 150.

Figure 9:
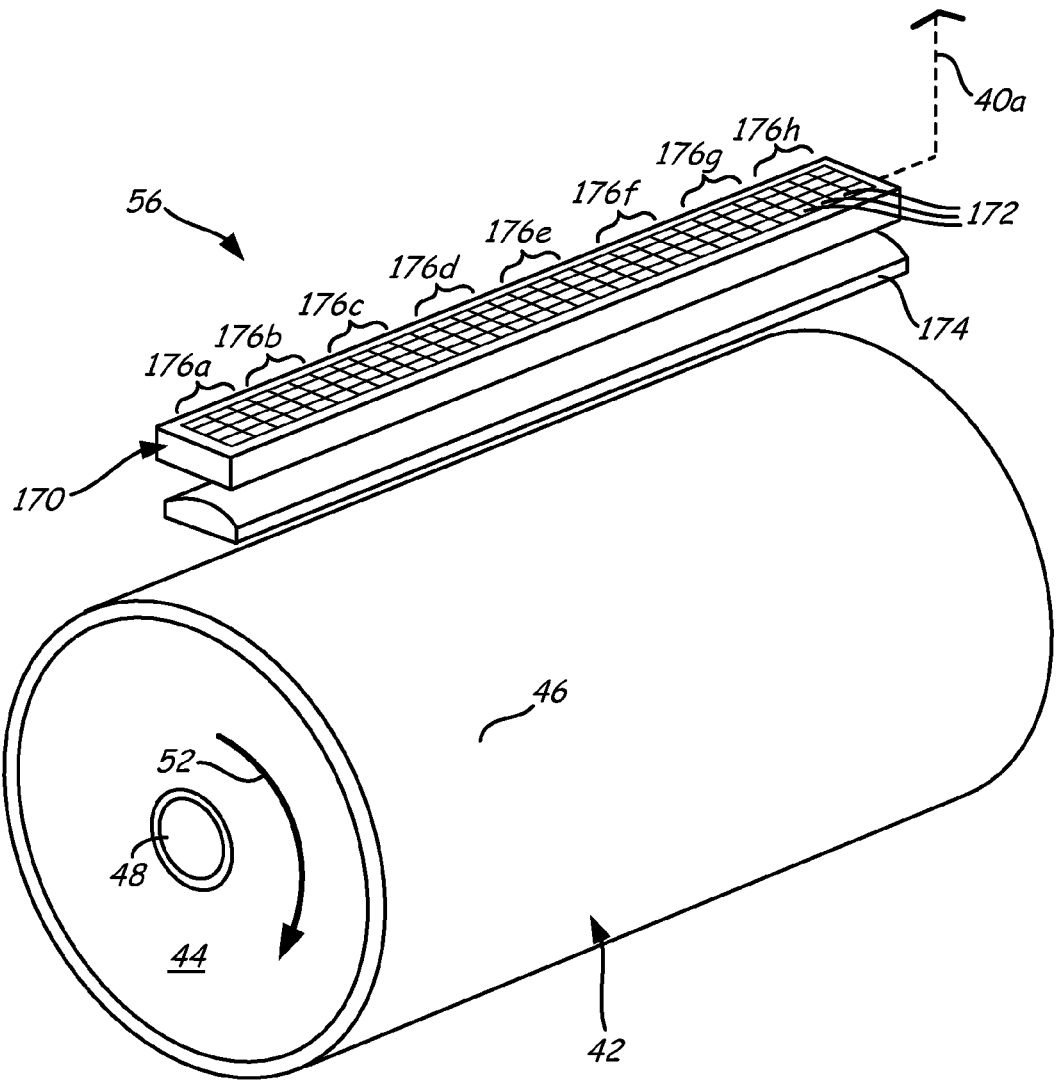
FIG. 9 is a front perspective view of a portion of an electrophotography engine, illustrating an imager and development drum of the electrophotography engine.

For example, as shown in FIG. 9, for each of EP engines 12p and 12s, imager 56 may include an LED array 170 having a plurality of individual LEDs 172, and optionally additional optics 174. During use, controller assembly 40 directs LED array 170 selectively illuminate the individual LEDs 172 with preset on-time durations, based on bitslices 160. This emits electromagnetic radiation toward the uniform electrostatic charge on surface 46 as surface 46 rotates in the direction of arrow 52 past imager 56.

This accordingly causes discrete pixel-wise locations of the electrostatic charge to be removed from surface 46 (i.e., discharged to ground), thereby forming latent image charge patterns on surface 46. In particular, the preset on-time durations affect the intensities of the charge patterns on surface 46, which correspondingly affects how much of part material 66p or support material 66s is attracted to surface 46, based on the Q/M of the given material. Accordingly, the preset on-time durations of LEDs 172 affect the powder densities of the part material 66p and support material 66s that are formed on surface 46 to produce layers 64p and 64s (and test samples 106p and 106s).

Therefore, based on any recognized fluctuations or drifts in the powder densities or M/A values from capacitance signal data 162, controller assembly 40 may modify imager data 168 of the on-time registers for LEDs 172 to assist in stabilizing the powder densities in the developed layers 64p and 64s. These modifications may be performed on a global scale, where the on-time duration for each LED 172 in LED array 170 may be modified by the same amount, such as to compensate for powder density drifts over time.

Alternatively, the LEDs 172 in LED array 170 may be grouped into blocks 176, such as blocks 176a-176h, each of which may correspond to one of the sensors 108 of detector 38 (or to multiple sensors 108). In this case, each block 176a-176h may be associated with one or more corresponding sensors 108a-108h, allowing controller assembly 40 to use each sensor 108 to modify the on-time duration for each LED 172 in the associated block 176 by the same amount. This can also compensate for powder density drifts over time, and provides greater control over LEDs 172 compared to the global modification to LED array 170.

Furthermore, controller assembly 40 may modify imager data 168 of the on-time registers for each individual LED 172 in LED array 170. This can provide high-resolution control over each individual LED 172 to compensate for a variety of powder density deviations.

In one embodiment, controller assembly 40 may modify the on-time durations for LEDs 172 during calibration routines, such as between printing operations and/or during the start of a printing operation. Additionally, controller assembly 40 may modify the on-time durations for LEDs 172 during a printing operation, such as with feedback control loops. This can assist in compensate for fluctuations or drifts in the powder densities, allowing real-time control over processing variations in system 10.

Although the present disclosure has been described with reference to preferred embodiments, workers skilled in the art will recognize that changes may be made in form and detail without departing from the spirit and scope of the disclosure.

The invention claimed is:

1. An additive manufacturing system for printing a three-dimensional part, the additive manufacturing system comprising:
   one or more electrophotography engines configured to develop one or more layers of the three-dimensional part;
   a rotatable transfer belt configured to receive the one or more developed layers from the one or more electrophotography engines;
   a detector configured to measure at least one parameter related to a powder density corresponding to one developed layer of the one or more developed layers on the rotatable transfer belt, and to transmit signals relating to the measured at least one parameter for at least one of the developed layers;
a printing assembly configured to receive the developed layer from the rotatable transfer belt and to print the three-dimensional part from the developed layers; and
a controller assembly configured to receive the transmitted signals from the detector, compare the received signals to a set point, and adjust one or more process parameters while developing one or more subsequent layers based on a difference between the received signals and the set point.

2. The additive manufacturing system of claim 1, wherein the detector comprises one or more capacitance sensors for measuring the at least one parameter for related to the powder density corresponding to one developed layer.

3. The additive manufacturing system of claim 2, wherein the one or more capacitance sensors comprise a plurality of capacitance sensors arranged in an array that is perpendicular to a movement direction of the rotatable transfer belt.

4. The additive manufacturing system of claim 2, wherein the detector further comprises a casing having one or more magnetic shielding materials, and which defines a slot for the rotatable transfer belt to move through, and wherein the one or more capacitance sensors are retained within the casing.

5. The additive manufacturing system of claim 2, wherein the detector further comprises a control board, and wherein each of the one or more capacitance sensors comprises:
an excitation electrode electrically connected to the control board;
a sense electrode electrically connected to the control board, and offset from the excitation electrode by a gap, wherein the rotatable transfer belt extends through the gap;
a first shield ground plate secured to the excitation electrode opposite of the gap; and
a second shield ground plate secured to the sense electrode opposite of the gap.

6. The additive manufacturing system of claim 5, and further comprising:
a first insulating film secured to the excitation electrode such that the first insulating film is located between the excitation electrode and the rotatable transfer belt; and
a second insulating film secured to the sense electrode such that the second insulating film is located between the sense electrode and the rotatable transfer belt.

7. The additive manufacturing system of claim 1, wherein the printing assembly comprises:
a heater configured to heat the developed layers;
a build platform; and
a pressing element configured to engage with the transfer assembly to press the heated developed layers into contact with a top surface of the three-dimensional part on the build platform in a layer-by-layer manner.

8. A method for printing a three-dimensional part with an additive manufacturing system, the method comprising:
producing a developed layer of a part material with an electrophotography engine of the additive manufacturing system;
transferring the developed layer from the electrophotography engine to a transfer belt of the additive manufacturing system;
rotating the transfer belt with the developed layer;
measuring a parameter related to a powder density of the developed layer on the rotating transfer belt with a detector;
transmitting signals related to the measured parameter related to the powder density of the developed layer to a controller assembly;
comparing the signals to a set point with the controller assembly;
heating the developed layer on the rotating transfer belt after measuring the powder density;
pressing the heated developed layer into contact with a top surface of the three-dimensional part; and
producing one or more subsequent developed layers by adjusting one or more process parameters based on a difference between the received signals and the set point.

9. The method of claim 8, wherein measuring the parameter related to the powder density of the developed layer on the rotating transfer belt comprises:
measuring one or more capacitance values of the developed layer on the rotating transfer belt;
transmitting signals relating to the one or more measured capacitance values for the developed layer to the controller assembly; and
determining a sample capacitance value with the controller assembly from the transmitted signals for the developed layer.

10. The method of claim 9, wherein measuring the parameter related to powder density of the developed layer on the rotating transfer belt further comprises:
measuring one or more capacitance values of the rotating transfer belt in a clean state;
transmitting signals relating to the one or more measured capacitance values for the belt to the controller assembly;
determining a baseline capacitance value with the controller assembly from the transmitted signals for the belt; and
determining a difference between the sample capacitance value and the baseline capacitance value with the controller assembly.

11. The method of claim 8, and further comprising modifying imager data for the electrophotography engine based on the measured powder density.

12. The method of claim 8, and further comprising measuring z-heights of the heated developed layer pressed on the three-dimensional part.

13. A method for measuring a capacitance of a developed layer, and utilizing the measured capacitance for adjusting one or more process parameters, in an additive manufacturing system, the method comprising:
rotating a transfer belt of the additive manufacturing system;
measuring one or more capacitance values of the rotating transfer belt in a clean state with a detector;
determining a baseline capacitance value from the one or more measured capacitance values for the rotating transfer belt;
producing the developed layer from a powder-based material with an electrophotography engine of the additive manufacturing system;
transferring the developed layer from the electrophotography engine to the rotating transfer belt;
measuring one or more capacitance values of the developed layer on the rotating transfer belt with the detector;
determining a sample capacitance value from the one or more measured capacitance values for the developed layer on the rotating transfer belt;

determining a difference between the sample capacitance value and the baseline capacitance value; and producing one or more subsequent developed layers by adjusting one or more process parameters based on the determined difference.

14. The method of claim 13, wherein producing the developed layer of the powder-based material comprises producing a test sample of the powder-based material for the developed layer, wherein the test sample has predetermined dimensions.

15. The method of claim 14, wherein measuring the one or more capacitance values of the developed layer on the rotating transfer belt comprises measuring one or more capacitance values of the test sample on the rotating transfer belt.

16. The method of claim 13, wherein measuring the one or more capacitance values of the developed layer on the rotating transfer belt comprises measuring a plurality of capacitance values of the of the developed layer on the rotating transfer belt with a plurality of capacitance sensors arranged in an array that extends perpendicular to a movement direction of the rotating transfer belt.

17. The method of claim 13, and further comprising insulating the plurality of capacitance sensors from spatially-varying potentials of the rotating transfer belt.

18. The method of claim 13, and further comprising modifying imager data for the electrophotography engine based on the determined difference between the sample capacitance value and the baseline capacitance value.

19. The method of claim 13, and further comprising modifying a triboelectric charge-to-mass (Q/M) ratio of the powder-based material based on the determined difference between the sample capacitance value and the baseline capacitance value.

* * * * *

UNITED STATES PATENT AND TRADEMARK OFFICE
CERTIFICATE OF CORRECTION

| | | |
|---|---|---|
| PATENT NO. | : 9,643,357 B2 | Page 1 of 1 |
| APPLICATION NO. | : 14/218114 | |
| DATED | : May 9, 2017 | |
| INVENTOR(S) | : Zeiter S. Farah and J. Samuel Batchelder | |

It is certified that error appears in the above-identified patent and that said Letters Patent is hereby corrected as shown below:

In the Claims

In Claim 16:
Please remove the words "of the" after the word "values" in line one of Column 22 so that the words "of the" only appear once.

Signed and Sealed this
Ninth Day of October, 2018

Andrei Iancu
*Director of the United States Patent and Trademark Office*